US00PP32282P2

(12) United States Plant Patent
Van Swieten

(10) Patent No.: US PP32,282 P2
(45) Date of Patent: Oct. 6, 2020

(54) *PHALAENOPSIS* ORCHID PLANT NAMED 'PHALGYTCAN'

(50) Latin Name: ***Phalaenopsis* hybrid**
Varietal Denomination: PHALGYTCAN

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/873,073

(22) Filed: Jan. 28, 2020

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALGYTCAN', particularly characterized by having white, flecked flowers with greenish-yellow and white lips, a convex flower shape, 1-to 4 peduncles, and is propagated by meristem tissue culture, is disclosed.

3 Drawing Sheets

Genus and species: *Phalaenopsis* hybrid.
Variety denomination: 'PHALGYTCAN'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGYTCAN'.

The new *Phalaenopsis* plant is a product of a planned breeding program conducted by the inventor in Bleiswijk, the Netherlands. The objective of this breeding program was to create a new *Phalaenopsis* plant with numerous attractive white, flecked flowers with greenish-yellow and white lips, suitable for potted plant production.

The new *Phalaenopsis* plant 'PHALGYTCAN' is a result of cross-pollination made by the inventor in July 2010 in Bleiswijk, the Netherlands, of the proprietary female, or seed parent, *Phalaenopsis* hybrid '22444-010' (unpatented) with the proprietary male, or pollen parent, *Phalaenopsis* hybrid '01-3177' (unpatented).

The new *Phalaenopsis* was selected by the inventor as a single plant within the progeny of the stated cross-pollination in a controlled greenhouse in Bleiswijk, the Netherlands, in April 2013. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 26, 2018 (Application number 20181199), by Applicant who obtained the subject matter disclosed directly from the inventor. 'PHALGYTCAN' has not been made publicly available or sold anywhere in the world prior to the effective filing date of this application with the exception of sales or disclosures made one year or less before the effective filing date of this claimed invention by Applicant who obtained 'PHALGYTCAN' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGYTCAN' as a new and distinct variety of *Phalaenopsis* plant:

1) White, flecked flowers with greenish-yellow and white lips;
2) Convex flower shape; and
3) 1 to 4 peduncles.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in December 2019. Colors in the photographs may differ from the color values cited in the detailed botanical description, which accurately describe the actual colors of the new variety.

DESCRIPTION OF THE NEW VARIETY

Figure 1:
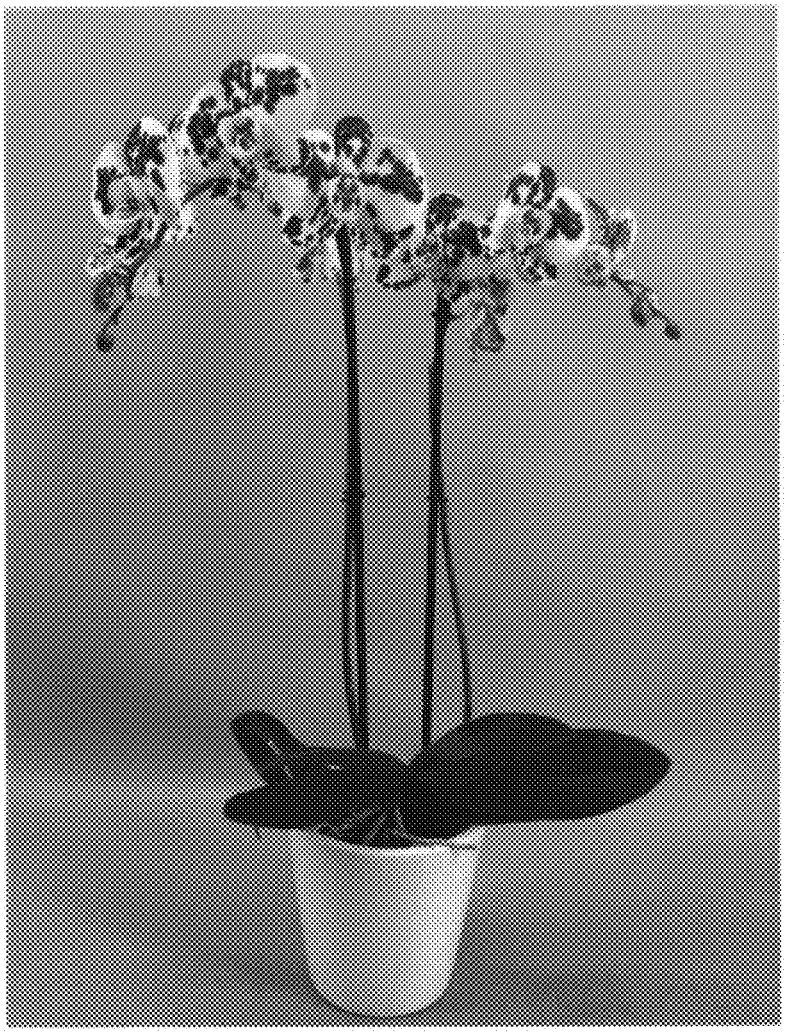
FIG. 1 shows the overall plant habit, including blooms, buds, and foliage of 'PHALGYTCAN'.
Figure 2:
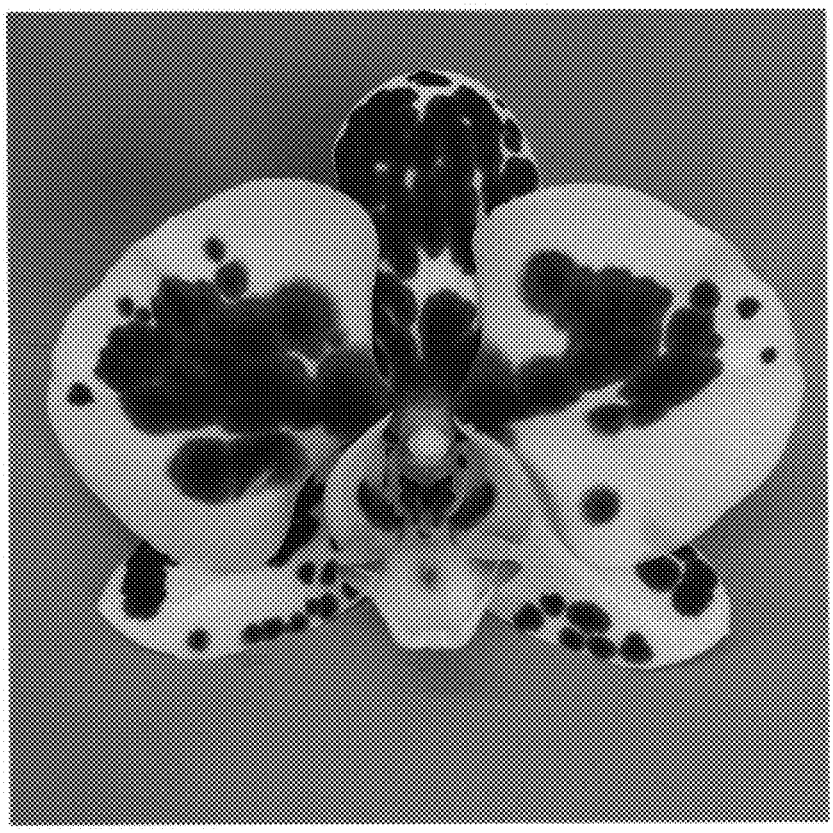
FIG. 2 shows a close-up of a flower of 'PHALGYTCAN'.
Figure 3:
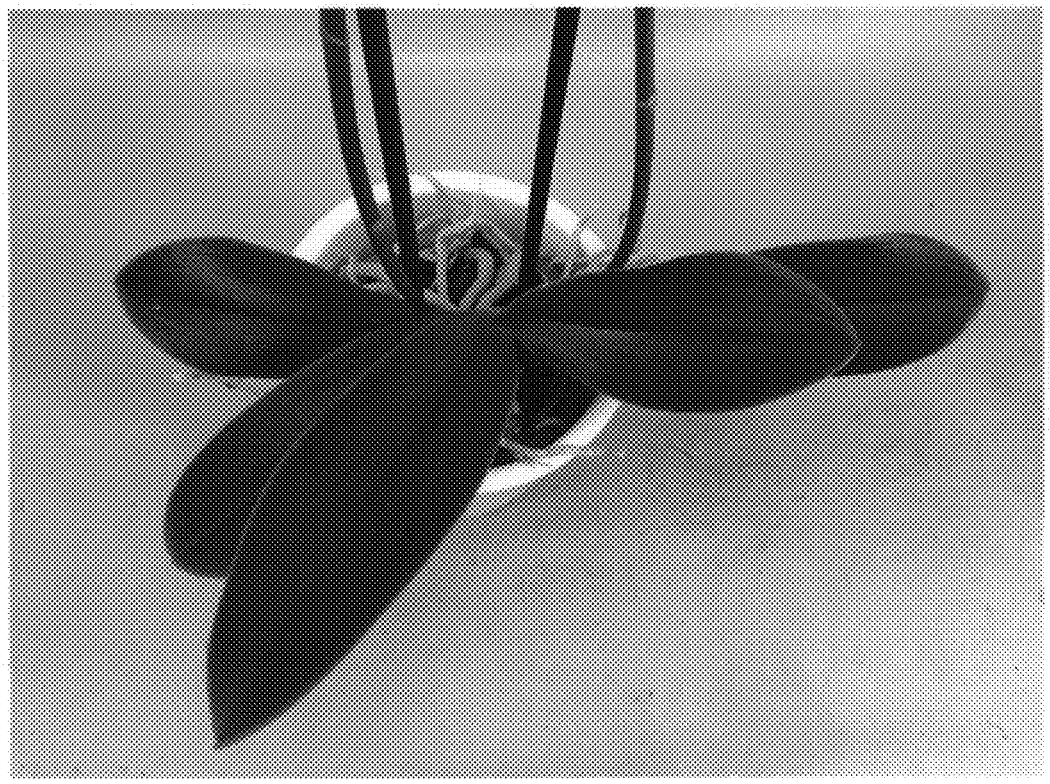
FIG. 3 shows an overhead view of the leaves of 'PHALGYTCAN'.

The following detailed description sets forth the distinctive characteristics of 'PHALGYTCAN'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in December 2019 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGYTCAN'.

Parentage:

*Female parent*.—*Phalaenopsis* cultivar '22444-010' (unpatented).

*Male parent*.—*Phalaenopsis* cultivar '01-3177' (unpatented).

Propagation:

*Type*.—Meristem tissue culture.

Roots:

*Root description*.—Greyed-green (between RHS 190B and 190C) colored roots with branching lateral roots having greenish-yellow (RHS 151A) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendant with raceme and panicle inflorescence.

*Height* (*from soil level to top of inflorescence*).—Approximately 58.0 cm to 63.0 cm.

*Width* (*measured from leaf tips*).—About 31.0 cm to 33.0 cm.

*Vigor*.—Strong.

Leaves:

*Mature leaves*.—Quantity per plant: 6 to 8 leaves are produced before flowering. Length (fully expanded): 16.0 cm to 18.0 cm. Width: 5.0 cm to 6.0 cm. Position of the broadest part of the leaf: Toward the apex. Shape: Obovate. Base shape: Moderately elongated. Apex: Unequal obtuse. Leaf blade angle with the petiole (measured from the horizontal position): Between 15 degrees and 30 degrees. Leaf margin: Entire. Color: Upper surface: RHS 146A. Lower surface: RHS 146B. Texture (both upper and lower surfaces): Smooth. Thickness: 2.7 mm to 3.0 mm. Variegation: Absent. Venation: Pattern: Parallel. Color of the midvein: Upper surface: RHS 146A. Lower surface: RHS 146B.

Peduncle:

*Quantity per plant*.—1 to 4.

*Number of flowers per peduncle*.—9 to 14.

*Length*.—58.0 cm to 63.0 cm.

*Diameter*.—5.0 mm to 5.5 mm.

*Strength*.—Strong.

*Aspect*.—Upright to slightly pendant.

*Texture*.—Smooth.

*Color*.—Green (RHS 146A).

*Internode length*.—3.0 cm to 4.0 cm.

Inflorescence description:

*Appearance*.—Upright to slightly pendant, raceme and panicle inflorescence with bilaterally symmetrical flowers that open in succession beginning with the lowermost flower.

*Number of inflorescences*.—1 to 4.

*Inflorescence size*.—Height (from base to tip): 210.0 mm to 310.0 mm.

*Flowering time*.—First flowers can be expected 10 to 11 months after planting in a 12-cm pot.

*Flower*.—Height: 77.0 mm to 82 0 mm. Diameter: 90.0 mm to 95.0 mm. Depth of lip: 22.0 mm to 24.0 mm.

*Flower longevity*.—On the plant: 10 to 14 weeks.

*Flower shape*.—Convex.

*Fragrance*.—Absent.

*Flower bud*.—Average size: Medium to large. Length: 21.0 mm to 23.0 mm. Width: 16.0 mm to 18.0 mm. Shape: Egg shaped. Color: Yellow-green (RHS N144D) flecked (RHS N77A).

*Petals*.—Arrangement: Open/free. Shape: Semi-circular. Apex: Slightly emarginated asymmetric. Margin: Moderately undulated. Length (from base to tip): 39.0 mm to 41.0 mm. Width: 50.0 mm to 52.0 mm. Position of the broadest part of the petal: Toward the base. Color (when fully opened): Upper surface: Basic color: White (RHS NN155C). Over color: Absent. Lower surface: Basic color: White (RHS NN155C). Over color: Diluting flecks (in the center RHS N79B and toward the margin RHS N79D). Number of spots and stripes on the petals (upper surface): Medium flecks. Color of spots and stripes on the petals (upper surface): Darker flecks (RHS 187B) in the center and lighter toward the margin (something between RHS N79C and N78A). Density of netting of the petals (upper surface): None. Color of the netting (upper surface): None.

*Dorsal sepal*.—Shape: Elliptic. Apex: Emarginated symmetric. Margin: Moderately undulated. Length (from base to tip): 48.0 mm to 50.0 mm. Width: 29.0 mm to 31.0 mm. Position of the broadest part of the dorsal sepals: In the middle. Color (when fully opened): Upper surface: Basic color: White (RHS NN155C). Over color: Absent Lower surface:. Basic color: White (RHS NN155C). Over color: Slightly light yellow-green (RHS 145C) in the middle with diluting flecks (RHS N79C and N77B). Number of spots and stripes on the dorsal sepals (upper surface): Many flecks. Color of spots and stripes on the dorsal sepals (upper surface): Darker flecks (RHS 187B) in the center and lighter toward the margin (RHS N79C). Density of netting of the dorsal sepals (upper surface): None. Color of the netting (upper surface): None.

*Lateral sepals*.—Shape: Ovate. Apex: Obtuse symmetric. Margin: Entire. Length (from base to tip): 45.0 mm to 47.0 mm. Width: 27.0 mm to 29.0 mm. Position of the broadest part of the lateral sepals: At the middle. Color (when fully opened): Upper surface: Basic color: White (RHS NN155C). Over color: Light yellow-green (RHS 145D) at the base. Lower surface: Basic color: White (RHS NN155C). Over color: Slightly light yellow-green (RHS 145C) in the middle; diluting flecks (in the center RHS N79B and toward the margin RHS N77B). Number of spots and stripes on the lateral sepals (upper surface): Medium flecks. Color of spots and stripes on the lateral sepals (upper surface): Darker flecks (RHS 187B) in the center and lighter toward the margin (RHS N79C). Density of netting of the lateral sepals (upper surface): None. Color of the netting (upper surface): None.

*Labellum* (*lip*).—Whiskers: Present. Length of whiskers: 24.0 mm to 26.0 mm. Color of whiskers: Light yellow (RHS 8D). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 21.0 mm to 23.0 mm. Width: 15.0 mm to 17.0 mm. Color: Upper surface: Red (RHS 184B) and dark reddish-orange (RHS 178B) at the base; greenish-yellow (RHS 5A) at one margin and white (RHS NN155C) toward the other margin. Lower surface: Slightly purplish-red (RHS N77D) at the base; greenish-yellow (RHS 5B) at one margin; white (RHS NN155C) toward the other margin. Number of spots and stripes on the lateral lobe (upper surface): None. Color of spots and stripes on the lateral lobe (upper surface): None. Density of netting of the lateral lobe (upper surface): None. Color of the netting (upper surface): None.

*Apical lobe*.—Shape: Triangular. Margin: Entire. Length: 23.0 mm to 25.0 mm. Width: 22.0 mm to 24.0 mm. Color: Upper surface: Hint of greenish-yellow (RHS 4A) at the base and toward wings; reddish-orange wings (RHS 176C) and red spot (RHS 183A) in the middle toward the base; white (RHS NN155C) towards whiskers. Lower surface: Greenish-yellow (RHS 4B) and reddish-orange wings (RHS 176D); diluting dark red spot (RHS N186C) in the middle toward the base; white (RHS NN155C) toward whiskers. Number of spots and stripes on the apical lobe (upper surface): None. Color of spots and stripes on the apical lobe (upper surface): None. Density of netting of the apical lobe (upper surface): None. Color of the netting (upper surface): None.

*Callus*.—Average size: Medium to large. Height: 7.0 mm to 8.0 mm. Length: 6.0 mm to 7.0 mm. Width: 4.0 mm to 5.0 mm. Color: Front side (RHS 184A); greenish-yellow (RHS 5B) upper side; yellowish-white (RHS 156D) on two sides; brown spots (RHS 200C and 200D).

Reproductive organs:

*Column*.—Length: 8.0 mm to 10.0 mm. Diameter: 5.8 mm to 6.3 mm. Color: Very light purple (RHS 76B); purple (RHS 77B) toward margins; white tip (RHS NN155C).

*Pollinia*.—Quantity: 2. Diameter: 1.0 mm to 1.3 mm. Color: Orange (RHS 24A).

*Ovary*.—Length: 10.0 mm to 12.0 mm. Diameter: 2.0 mm to 3.0 mm.

*Pedicel*.—Length: 33.0 mm to 35.0 mm. Diameter: 2.0 mm to 3.0 mm. Texture: Smooth. Color: Purplish-red (RHS N77D) at the base and yellow-green (RHS 145C to 145D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGYTCAN' differs from female parent plant '22444-010' (unpatented) in that 'PHALGYTCAN' has flowers with a flecked pattern, whereas '22444-010' has flowers with an even pattern. Additionally, 'PHALGYTCAN' has larger flowers than '22444-010'.

'PHALGYTCAN' differs from male parent plant '01-3177' (unpatented) in that 'PHALGYTCAN' has a medium curvature of the lateral lobe, whereas '01-3177' has a strong curvature of the lateral lobe.

'PHALGYTCAN' is most similar to the commercial *Phalaenopsis* plants named 'PHALDUZAH' (U.S. Plant Pat. No. 26,830) and 'PHALDISAM' (U.S. Plant Pat. No. 27,203). 'PHALGYTCAN' differs from the commercial variety 'PHALDUZAH' in that 'PHALGYTCAN' has longer dorsal sepals, narrower petals, and narrower leaves than 'PHALDUZAH'.

'PHALGYTCAN' differs from the commercial variety 'PHALDISAM' in that 'PHALGYTCAN' has longer dorsal sepals and wider petals than 'PHALDISAM'.

I claim:

1. A new and distinct variety of *Phalaenopsis* plant named 'PHALGYTCAN', substantially as described arid illustrated herein.

* * * * *